United States Patent [19]

Matsuo et al.

[11] Patent Number: 5,654,400

[45] Date of Patent: Aug. 5, 1997

[54] PROCESS FOR MAKING PEPTIDE COMPOUNDS HAVING TACHYKININ ANTAGONISTIC ACTIVITY

[75] Inventors: Masaaki Matsuo, Toyonaka; Daijiro Hagiwara, Moriguchi; Hiroshi Miyake, Kyoto, all of Japan

[73] Assignee: Fujisawa Pharmaceutical Co., Ltd., Osaka, Japan

[21] Appl. No.: 699,055

[22] Filed: Aug. 9, 1996

Related U.S. Application Data

[63] Continuation of Ser. No. 307,793, filed as PCT/JP93/00470, Apr. 9, 1993, abandoned, which is a continuation-in-part of Ser. No. 871,723, Apr. 21, 1992, Pat. No. 5,420,297, which is a continuation-in-part of Ser. No. 770,866, Oct. 4, 1991, abandoned.

[51] Int. Cl.$^6$ ............................ C07K 1/107; C07K 1/113
[52] U.S. Cl. ........................... 530/345; 548/525; 548/468
[58] Field of Search .................. 530/345; 514/19; 548/525, 468

[56] References Cited

U.S. PATENT DOCUMENTS

| | | | |
|---|---|---|---|
| 5,164,372 | 11/1992 | Matsuo et al. | 514/19 |
| 5,420,297 | 5/1995 | Matsuo et al. | 548/525 |
| 5,468,731 | 11/1995 | Matsuo et al. | 514/18 |

*Primary Examiner*—Cecilia J. Tsang
*Assistant Examiner*—Bennett Celsa
*Attorney, Agent, or Firm*—Oblon, Spivak, McClelland, Maier & Neustadt, P.C.

[57] ABSTRACT

A method of making a peptide compound of the formula:

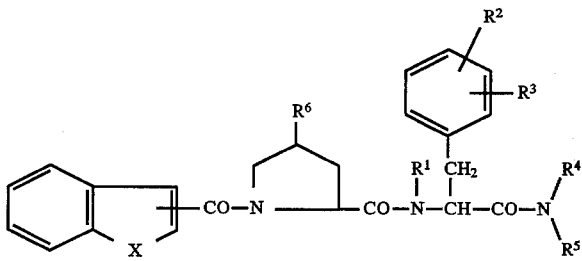

wherein
 $R^1$ is hydrogen or lower alkyl,
 $R^2$ is lower alkyl or halogen,
 $R^3$ is hydrogen, lower alkyl or halogen,
 $R^4$ is lower alkyl,
 $R^5$ is ar(lower)alkyl,
 $R^6$ is amino or optionally protected hydroxy, and
 X is O, S or N—$R^7$, in which $R^7$ is N,N-di(lower)alkylamino(lower)alkyl,
which is useful as tachykinin antagonist.

1 Claim, No Drawings

PROCESS FOR MAKING PEPTIDE COMPOUNDS HAVING TACHYKININ ANTAGONISTIC ACTIVITY

DESCRIPTION

This is a continuation of application Ser. No. 08/307,793 filed on Oct. 17, 1994, now abandoned; which is a national stage PCT application of International Application No. PCT/JP93/00470 filed on Apr. 9, 1993 which designated the U.S. as a continuation-in-part application of U.S. Ser. No. 07/871,723 filed Apr. 21, 1992, now U.S. Pat. No. 5,420,297 which is a CIP of Ser. No. 07/770,866 filed Oct. 14, 1991 which is abandoned.

TECHNICAL FIELD

The present invention relates to new peptide compounds and pharmaceutically acceptable salt thereof.

More particularly, it relates to new peptide compounds and pharmaceutically acceptable salts thereof which have pharmacological activities such as tachykinin antagonism, especially substance P antagonism, neurokinin A antagonism, neurokinin B antagonism, and the like, to processes for preparation thereof, to pharmaceutical composition comprising the same, and to a use of the same as a medicament.

DISCLOSURE OF THE INVENTION

One object of the present invention is to provide new and useful peptide compounds and pharmaceutically acceptable salts thereof which have pharmacological activities such as tachykinin antagonism, especially substance P antagonism, neurokinin A antagonism, neurokinin B antagonism, and the like.

Another object of the present invention is to provide processes for the preparation of said peptide compounds and salts thereof.

A further object of the present invention is to provide a pharmaceutical composition comprising, as an active ingredient, said peptide compounds and pharmaceutically acceptable salts thereof.

Still further object of the present invention is to provide a use of said peptide compound or a pharmaceutically acceptable salt thereof as tachykinin antagonist, especially substance P antagonist, neurokinin A antagonist or neurokinin B antagonist, useful for treating or preventing tachykinin mediated diseases, for example, respiratory diseases such as asthma, bronchitis, rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g., migraine, headache, toothache, cancerous pain, back pain, etc.); and the like in human being or animals.

The object compounds of the present invention can be represented by the following general formula (I).

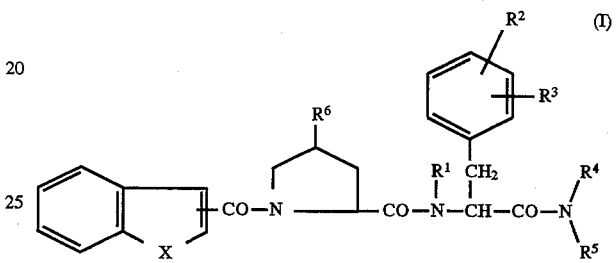

wherein $R^1$ is hydrogen or lower alkyl, $R^2$ is lower alkyl or halogen, $R^3$ is hydrogen, lower alkyl or halogen, $R^4$ is lower alkyl, $R^5$ is ar(lower)alkyl, $R^6$ is amino or optionally protected hydroxy, and X is O, S or N—$R^7$, in which $R^7$ is N,N-di(lower)alkylamino(lower)alkyl.

According to the present invention, the new peptide compounds (I) can be prepared by processes which are illustrated in the following schemes.

Process 1

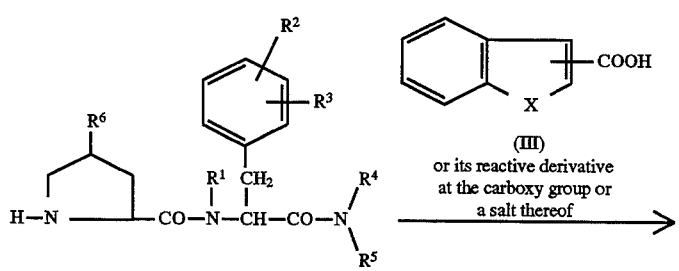

(II)
or its reactive derivative
at the amino group or
a salt thereof

-continued
Process 1
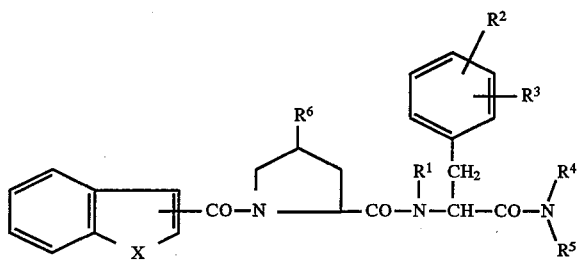
(I)
or a salt thereof
Process 2
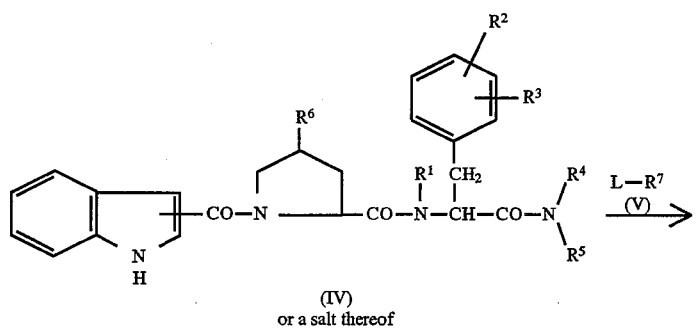
(IV)
or a salt thereof
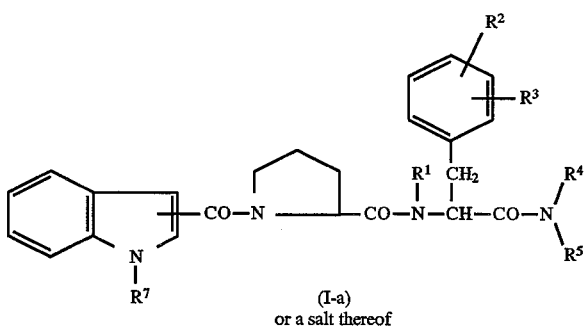
(I-a)
or a salt thereof
Process 3
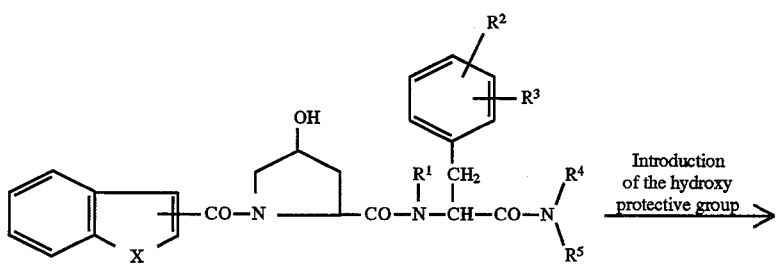
(I-b)
or its reactive derivative at the
hydroxy group of a salt thereof -continued Process 3

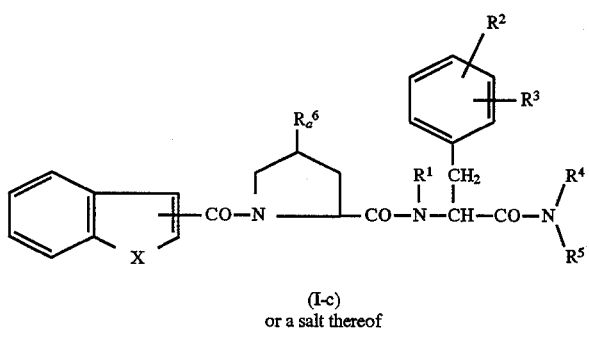

(I-c)
or a salt thereof

Process 4

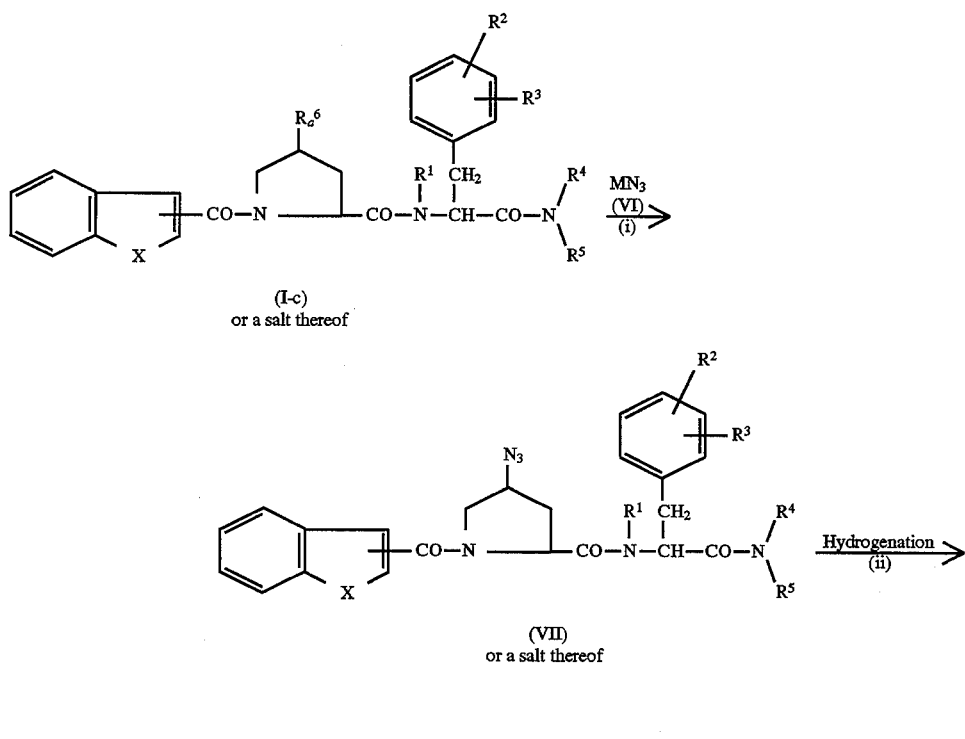

(I-d)
or a salt thereof wherein $R^1$, $R^2$, $R^3$, $R^4$, $R^5$, $R^6$, $R^7$ and X are each as defined above, $R_a^6$ is protected hydroxy, L is an acid residue, and M is an alkaline metal.

As to the starting compounds (II), (III) and (IV), some of them are novel and can be prepared by the procedures described in the preparations and Examples mentioned later or a conventional manner.

Throughout the present specification, the amino acid, peptides, protective groups, condensing agents, etc. are indicated by the abbreviations according to the IUPAC-IUB (Commission on Biological Nomenclature) which are in common use in the field of art.

Moreover, unless otherwise indicated, the amino acids and their residues when shown by such abbreviations are meant to be L-configured compounds and residues.

Suitable pharmaceutically acceptable salts of the starting and object compound are conventional non-toxic salt and include an acid addition salt such as an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydriodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention include within the scope thereof are explained in detail as follows.

The term "lower" is intended to mean 1 to 6, preferably 1 to 4 carbon atom(s), unless otherwise indicated.

Suitable "lower alkyl" may include a straight or branched one such as methyl, ethyl, propyl, isopropyl, butyl, isobutyl, tert-butyl, pentyl, hexyl, and the like, in which the most preferred one is methyl.

Suitable "alkaline metal" may include sodium, potassium, and the like.

Suitable "an acid residue" may include halogen (e.g., fluoro, chloro, bromo, iodo), acyloxy (e.g., tosyloxy, mesyloxy, etc.), and the like.

Suitable "ar(lower)alkyl" may include a conventional group, which is used in the field of amino acid and peptide chemistry, such as mono- or di- or triphenyl(lower)alkyl (e.g. trityl, benzhydryl, benzyl, phenethyl, etc.), and the like.

The term "halogen" means fluoro, chloro, bromo, iodo.

Suitable "optionally protected hydroxy" means that the hydroxy group may be protected by a conventional protective group such as acyl (e.g. acetyl, mesyl, etc.), and the like.

Suitable "N,N-di(lower)alkylamino(lower)alkyl" may include N,N-dimethylaminomethyl, N,N-dimethylaminoethyl, and the like.

Particularly, the preferred embodiments of $R^1$, $R^2$, $R^3$, $R^4$, $R^5$, $R^6$ and X are as follows.

$R^1$ is hydrogen; or lower alkyl (e.g. methyl, etc.), $R^2$ is lower alkyl (e.g. methyl, t-butyl, etc.); or halogen (e.g. chloro, etc.), $R^3$ is hydrogen; lower alkyl (e.g. methyl, etc.); or halogen (e.g. chloro, etc.), $R^4$ is lower alkyl (e.g. methyl, etc.), $R^5$ is mono- or di- or triphenyl(lower)alkyl (e.g. benzyl, etc.), $R^6$ is amino; or hydroxy, and X is O; S; or N—$R^7$, in which $R^7$ is N,N-di(lower)alkylamino(lower)alkyl (e.g. N,N-dimethylaminoethyl, etc.).

The processes for preparing the object compound are explained in detail in the following.

Process 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsyliy) acetamide, bis(trimethylsilyl)urea or the like; a derivative formed by reaction of the compound (II) with phosphorus trichloride or phosgene, and the like.

Suitable salts of the compound (II) and its reactive derivative can be referred to the ones as exemplified for the compound (I).

Suitable reactive derivative at the carboxy group of the compound (III) may include an acid halide, an acid anhydride, an activated amide, an activated ester, and the like. Suitable examples of the reactive derivatives may be an acid chloride; an acid azide;.a mixed acid anhydride within acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+=CH—$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

Suitable salts of the compound (III) and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], or the like, and an acid addition salt as exemplified for the compound (I).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine;

ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; benzotriazol-1-yl-oxy-tris-(dimethylamino)phosphoniumhexafluorophosphate; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 2

The object compound (I-a) or a salt thereof can be prepared by reacting the compound (IV) or a salt thereof with the compound (V).

The present reaction is usually carried out in the presence of a base such as alkali lithium (e.g. n-butyl lithium, etc.), alkali metal hydride (e.g. sodium hydride, potassium hydride, etc.), tri(lower)alkylamine (e.g. trimethylamine, triethylamine, etc.), pyridine or its derivative (e.g. picoline, lutidine, 4-dimethylaminopyridine, etc.), or the like.

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the base to be used is liquid, it can also be used as a solvent.

If necessary, the present reaction can be used phase transfer catalyst (e.g. cetyltrimethylammonium chloride, etc.).

The reaction temperature is not critical and the reaction is usually carried out under cooling, at ambient temperature or under heating.

Process 3

The object compound (I-c) or a salt thereof can be prepared by subjecting the compound (I-b) or its reactive derivative at the hydroxy group or a salt thereof to introduction reaction of the hydroxy protective group.

The reaction can be carried out in substantially the same manner as Process 1, and therefore the reaction mode and reaction conditions [e.g. solvents, reaction temperature, etc.] of this reaction are to be referred to those as explained in Process 1.

Process 4-(i)

The compound (VII) or a salt thereof can be prepared by reacting the compound (I-c) or a salt thereof with the compound (VI).

The reaction is usually carried out in a conventional solvent such as dimethyl sulfoxide or any other solvent which does not adversely influence the reaction.

The reaction temperature is not critical and the reaction is usually carried out under warming to heating.

Process 4-(ii)

The object compound (I-d) or a salt thereof can be prepared by subjecting the compound (VII) or a salt thereof to hydrogenation. This reaction is usually carried out in the presence of triphenylphosphine, palladium on carbon, or the like.

The reaction is usually carried out in a conventional solvent such as alcohol (e.g., methanol, ethanol, etc.), or any other solvent which does not adversely influence the reaction.

The reaction temperature is not critical and the reaction is usually carried out under cooling to heating.

The compounds obtained by the above processes can be isolated and purified by a conventional method such as pulverization, recrystallization, column chromatography, reprecipitation, or the like.

It is to be noted that the compound (I) and the other compounds may include one or more stereoisomers due to asymmetric carbon atoms, and all of such isomers and mixture thereof are included within the scope of this invention.

The object compounds (I) and pharmaceutically acceptable salt thereof have pharmacological activities such as tachykinin antagonism, especially substance P antagonism, neurokinin A antagonism or neurokinin B antagonism, and therefore are useful for treating or preventing tachykinin mediated diseases, for example, respiratory diseases such as asthma, bronchitis rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g. migraine, headache, toothache, cancerous pain, back pain, etc.); and the like.

Further, it is expected that the object compounds (I) of the present invention are useful for treating or preventing ophthalmic diseases such as glaucoma, uveitis, and the like; gastrointestinal diseases such as ulcer, ulcerative colitis, irritable bowel syndrome, food allergy, and the like; inflammatory diseases such as nephritis, and the like; circulatory diseases such as hypertension, angina pectoris, cardiac failure, thrombosis, and the like; epilepsy; spartic paralysis; pollakiuria; dementia; Alzheimer's diseases; schizophrenia; Huntington's chorea; carcinoid syndrome; and the like, and useful for immunosuppresive agent.

For therapeutic purpose, the compounds (I) and pharmaceutically acceptable salts thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral, external, enteral, intravenous, intramuscular, inhalant, nasal or intraarticular administration. The pharmaceutical preparations may be capsules, tablets, dragees, granules, solution, suspension, emulsion, ointment, or the like. If desired, there may be included in these preparation, auxiliary substances, stabilizing agents, wetting or emulsifying agents, buffers and other commonly used additives.

While the dosage of the compounds (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating asthma and the like. In general, amounts between 0.1 mg/body and about 1,000 mg/body may be administered per day.

In order to illustrate the usefulness of the object compound (I), the pharmacological test data of some representative compound of the compound (I) is shown in the following.

Test Compound:

(a)

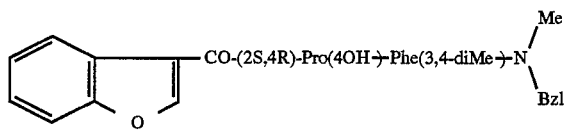

(1) ³H-Substance P receptor binding
Test Method:
  (a) Crude Lung Membrane Preparation
  Male Hartly strain guinea pigs were sacrificed by decapitation. The trachea and lung were removed and homogenized in buffer (0.25M sucrose, 50 mM Tris-HCl pH 7.5, 0.1 mM EDTA) by suing Polytoron (Kinematica). The homogenate was centrifuged (1000 xg, 10 min) to remove tissue clumps and the supernatant was centrifuges (14000 xg 20 min) to yield pellets. The pellets were resuspended in buffer (5 mM Tris-HCl pH 7.5), homogenized with a teflon homogenizer and centrifuged (14000 xg, 20 min) to yield pellets which were referred to as crude membrane fractions. The obtained pallets were stored at −70° C. until use.
  (b) ³H-Substance P Binding to Preparation Membrane
  Frozen crude membrane fractions were thawed and resuspended in Medium 1 (50 mM Tris-HCl pH 7.5, 5 mM MnCl$_2$, 0.02% BSA, 2 µg/ml chymostatin, 4 µg/ml leupeptin, 40 µg/ml bacitracin.) ³H-substance P (1 nM) was incubated with 100 µl of the membrane preparation in Medium 1 at 4° C. for 30 minutes in a final volume of 500 µl. At the end of the incubation period, reaction mixture was quickly filtered over a Whatman GF/B glass filter (pretreated with 0.1% polyethylene imine for 3 hours prior to use) under aspiration. The filters were then washed four times with 5 ml of the buffer (50 mM Tris-HCl, pH 7.5). The radioactivity was counted in 5 ml of Aquazol-2 in Packerd scintillation counter (Packerd TRI -CARB 4530).

Test Result:

| Test Compound (0.1 µg/ml) | Inhibition (%) |
|---|---|
| (a) | 96.3 |

The following examples are given for purpose of illustrating the present invention in detail.

In these examples, there are employed the following abbreviations in addition to the abbreviations adopted by the IUPAC-IUB.
  Ac: acetyl
  Boc: t-butoxycarbonyl
  Bu$^t$: t-butyl
  Bzl: benzyl
  DMF: dimethylformamide
  DMSO: dimethylsulfoxide
  HOBT: N-hydroxybenzotriazole
  Me: methyl
  Ms mesyl
  HCl/DOX: hydrogen chloride in 1,4-dioxane
  TEA: triethylamine
  TFA: trifluoroacetic acid
  THF: tetrahydrofuran
  WSC: 1-ethyl-3-(3'-dimethylaminopropyl)-carbodiimide The Starting Compounds used and the Object Compounds obtained in the following examples are given in The Table as below, in which the formulae of the former compounds are in the upper and the formulae of the latter compounds are in the lower, respectively.

TABLE

| Preparation No. | Formula |
|---|---|
| 1 | H—Phe(3,4-diMe)—OH |
|   | Boc—Phe(3,4-diMe)—OH |
| 2 | Boc—Phe(3,4-diMe)—OH |
|   | Boc—Phe(3,4-diMe)—N(Me)(Bzl) |
| 3 | Boc—Phe(3,4-diMe)—N(Me)(Bzl) |
|   | HCl.H—Phe(3,4-diMe)—N(Me)(Bzl) |
| 4 | HCl.H—Phe(3,4-diMe)—N(Me)(Bzl) |

TABLE-continued

| | Formula |
|---|---|
| | Boc—(2S,4R)—Pro(4OH)—Phe(3,4-diMe)—N(Me)(Bzl) |
| 5 | Boc—(2S,4R)—Pro(4OH)—Phe(3,4-diMe)—N(Me)(Bzl) |
| | TFA.H—(2S,4R)—Pro(4OH)—Phe(3,4-diMe)—N(Me)(Bzl) |
| 6 | Ac—Phe(3,4-diCl)—OH |
| | H—Phe(3,4-diCl)—OH |
| 7 | Boc—Phe(3,4-diMe)—OH |
| | Boc—MePhe(3,4-diMe)—OH |
| 8 | H—Phe(3,4-diCl)—OH |
| | Boc—Phe(3,4-diCl)—OH |
| 9 | Boc—Phe(3,4-diCl)—OH |
| | Boc—Phe(3,4-diCl)—N(Me)(Bzl) |
| 10 | Boc—MePhe(3,4-diMe)—OH |
| | Boc—MePhe(3,4-diMe)—N(Me)(Bzl) |
| 11 | Boc—Phe(3,4-diCl)—N(Me)(Bzl) |
| | Boc—(2S,4R)—Pro(4OH)—Phe(3,4-diCl)—N(Me)(Bzl) |
| 12 | Boc—MePhe(3,4-diMe)—N(Me)(Bzl) |
| | HCl.H—MePhe(3,4-diMe)—N(Me)(Bzl) |
| 13 | HCl.H—MePhe(3,4-diMe)—N(Me)(Bzl) |
| | Boc—(2S,4R)—Pro(4OH)—MePhe(3,4-diMe)—N(Me)(Bzl) |
| 14 | Boc—(2S,4R)—Pro(4OH)—Phe(3,4-diCl)—N(Me)(Bzl) |

TABLE-continued

| | Formula |
|---|---|
| | HCl.H—(2S,4R)—Pro(4OH)—Phe(3,4-diCl)—N(Me)(Bzl) |
| 15-(1) | H—Phe(p-Me)—OH |
| | Boc—Phe(p-Me)—OH |
| 15-(2) | H—Phe(p-Bu$^t$)—OH |
| | Boc—Phe(p-Bu$^t$)—OH |
| 16-(1) | Boc—Phe(p-Me)—OH |
| | Boc—Phe(p-Me)—N(Me)(Bzl) |
| 16-(2) | Boc—Phe(p-Bu$^t$)—OH |
| | Boc—Phe(p-Bu$^t$)—N(Me)(Bzl) |
| 17-(1) | Boc—Phe(p-Me)—N(Me)(Bzl) |
| | HCl.H—Phe(p-Me)—N(Me)(Bzl) |
| 17-(2) | Boc—Phe(p-Bu$^t$)—N(Me)(Bzl) |
| | HCl.H—Phe(p-Bu$^t$)—N(Me)(Bzl) |
| 18-(1) | HCl.H—Phe(p-Me)—N(Me)(Bzl) |
| | Boc—(2S,4R)—Pro(4OH)—Phe(p-Me)—N(Me)(Bzl) |
| 18-(2) | HCl.H—Phe(p-Bu$^t$)—N(Me)(Bzl) |
| | Boc—(2S,4R)—Pro(4OH)—Phe(p-Bu$^t$)—N(Me)(Bzl) |
| 19 | Boc—(2S,4R)—Pro(4OH)—Phe(p-Me)—N(Me)(Bzl) |

TABLE-continued

| | Formula |
|---|---|
| | HCl.H—(2S,4R)—Pro(4OH)—Phe—(p-Me)—N(Me)(Bzl) |
| 20 | Boc—(2S,4R)—Pro(4OH)—Phe(p-Bu$^t$)—N(Me)(Bzl) |
| | HCl.H—(2S,4R)—Pro(4OH)—Phe(p-Bu$^t$)—N(Me)(Bzl) |

| Example No. | |
|---|---|
| 1 | Boc—(2S,4R)—Pro(4OH)—MePhe(3,4-diMe)—N(Me)(Bzl) |
| |  indol-3-yl with N-(CH$_2$)$_2$NMe$_2$ —CO—(2S,4R)—Pro(4OH)—MePhe(3,4-diMe)—N(Me)(Bzl) · HCl |
| 2 | HCl.H—(2S,4R)—Pro(4OH)—Phe(3,4-diCl)—N(Me)(Bzl) |
| |  benzofuran-2-yl—CO—(2S,4R)—Pro(4OH)—Phe(3,4-diCl)—N(Me)(Bzl) |
| 3 | TFA.H—(2S,4R)—Pro(4OH)—Phe(3,4-diMe)—N(Me)(Bzl) |
| |  benzofuran-2-yl—CO—(2S,4R)—Pro(4OH)—Phe(3,4-diMe)—N(Me)(Bzl) |
| 4-(1) | HCl.H—(2S,4R)—Pro(4OH)—Phe(p-Me)—N(Me)(Bzl) |
| |  benzofuran-2-yl—CO—(2S,4R)—Pro(4OH)—Phe(p-Me)—N(Me)(Bzl) |
| 4-(2) | HCl.H—(2S,4R)—Pro(4OH)—Phe(p-Bu$^t$)—N(Me)(Bzl) |

TABLE-continued

| | Formula |
|---|---|
| | benzofuran-2-yl—CO—(2S,4R)—Pro(4OH)—Phe(p-Bu$^t$)—N(Me)(Bzl) |
| 4-(3) | TFA.H—(2S,4R)—Pro(4OH)—Phe(3,4-diMe)—N(Me)(Bzl) |
| | benzothiophen-2-yl—CO—(2S,4R)—Pro(4OH)—Phe(3,4-diMe)—N(Me)(Bzl) |
| 5 | benzofuran-2-yl—CO—(2S,4R)—Pro(4OH)—Phe(3,4-diMe)—N(Me)(Bzl) |
| | benzofuran-2-yl—CO—(2S,4R)—Pro(4OMs)—Phe(3,4-diMe)—N(Me)(Bzl) |
| 6 | benzofuran-2-yl—CO—(2S,4R)—Pro(4OMs)—Phe(3,4-diMe)—N(Me)(Bzl) |
| | benzofuran-2-yl—CO—(2S,4R)—Pro(4HH$_2$)—Phe(3,4-diMe)—N(Me)(Bzl) |

Preparation 1

To a suspended mixture of Starting Compound (20.0 g) in a mixed solvent of water (200 ml) and acetone (50 ml) was added TEA (31.8 ml) under ice-cooling. To the solution was added a solution of di-tert-butyldicarbonate (27.9 g) in acetone (50 ml), and the solution was stirred at room temperature for 2.5 hours. After removal of the acetone, water was added and the aqueous solution was washed once with ether. The aqueous layer was then acidified to pH 2 with an addition of 6N hydrochloric acid and was extracted with ethyl acetate. The extract was washed with an aqueous sodium chloride solution and was dried over magnesium sulfate. After evaporation, the residue was collected by filtration and dried to give Object Compound (23.4 g).

IR (CHCl$_3$): 3470, 1725, 1715, 1500 cm$^{-1}$

NMR (DMSO-d$_6$, δ): 1.33 (9H, s), 2.17 (6H, s), 2.65–3.0 (2H, m), 3.95–4.1 (1H, m), 6.9–7.05 (4H, m), 12.46 (1H, br s)

Preparation 2

Starting Compound (21.9 g) and TEA (11.4 ml) was dissolved in methylene chloride (200 ml). The solution was ice-cooled and pivaloyl chloride (9.88 g) was added dropwise and the resulting solution was stirred for 30 minutes at this temperature. Then N-methylbenzylamine (9.6 ml) was added to this solution during twelve minutes at this temperature. The reaction mixture was stirred for additional an hour at this temperature and for further an hour at room temperature. The solution was washed successively with water, sodium hydrogen carbonate solution, water, 1N hydrochloric acid and brine, and dried over magnesium sulfate. Evaporation of the solvent gave Object Compound as an oil (30.7 g).

IR (Neat): 3450, 3320, 1710, 1640, 1365 cm$^{-1}$

NMR (DMSO-d$_6$, δ): 1.2–1.4 (9H, m), 2.1–2.2 (6H, m), 2.65–2.95 (5H, m), 4.3–4.7 (3H, m), 6.75–7.4 (9H, m)

Preparation 3

To an ice-cooled solution of Starting Compound (30.5 g) in ethyl acetate (152 ml) was added 4N hydrochloric acid (192 ml) in ethyl acetate. The solution was stirred at this temperature for ten minutes and additional at room temperature one and half an hour. Insoluble materials were filtered off and the filtrate was concentrated under reduced pressure. The residue was crystallized with a mixed solvent of ether (100 ml) and ethyl acetate (6 ml) under ice-cooling. The crystalline materials were collected by filtration, dried to give Object Compound (19.5 g).

mp: 96°–104° C.

IR (Nujol): 3440, 1650, 1610, 1490, 1450, 1280 cm$^{-1}$

NMR (DMSO-d$_6$, δ): 2.1–2.25 (6H, m), 2.62 (s) and 2.69 (3H, s), 2.85–3.2 (2H, m), 4.0–4.1 and 4.35–4.65 (3H, m), 6.9–7.4 (8H, m), 8.49 (3H, br s)

Preparation 4

To an ice-cooled solution of Starting Compound (12.1 g), Boc-(2S,4R)-Pro(4OH)-OH (17.4 g) and HOBT (7.06 g) in methylene chloride (120 ml) was added WSC (8.06 g). The solution was stirred at the same temperature for an hour and at room temperature overnight. After evaporation, the reaction mixture was extracted with ethyl acetate and the organic layer was washed successively with an aqueous sodium hydrogencarbonate solution, water, 0.5N hydrochloric acid, water and an aqueous sodium chloride solution, and was dried over magnesium sulfate. Evaporation gave the Object Compound (27.4 g) as an amorphous solid.

IR (CHCl$_3$): 3450–3300, 1690–1650, 1645–1625, 1450, 1155 cm$^{-1}$

NMR (DMSO-d$_6$, δ): 1.2–1.45 (9H, m), 1.6–1.85 (1H, m), 1.9–2.2 (7H, m), 2.7–3.0 (5H, m), 3.15–3.5 (2H, m), 4.1–5.1 (6H, m), 6.7–7.35 (8H, m), 8.25–8.35 (1H, m)

Preparation 5

To an ice-cooled solution of Starting Compound (27 g) in methylene chloride (54 ml) was added trifluoroacetic acid (136 ml). The solution was stirred at the same temperature for ten minutes and at room temperature for forty minutes. After evaporation, the residue was crystallized with ether, collected by filtration and dried to give Object Compound (0.90 g).

mp: 164°–167° C.

IR (CHCl$_3$): 3450–3200, 1680, 1640, 1565, 1455 cm$^{-1}$

NMR (DMSO-d$_6$, δ): 1.7–1.9 (1H, m), 2.1–2.4 (7H, m), 2.65–3.15 (5H, m), 3.25–3.5 (2H, m), 4.2–5.1 and 5.55–5.65 (6H, m), 6.8–7.4 (8H, m), 9.1–9.3 (1H, m), 8.65 (1H, br s), 10.0 (1H, br s)

Preparation 6

To a suspended mixture of Starting Compound (18.0 g) in water (90 ml) was added 1N aqueous sodium hydroxide solution (65.8 ml). The solution was warmed to 37° C. and the pH was adjusted to 8.0 by an addition of 1N hydrochloric acid. Then cobalt(II) chloride hexahydrate (90 mg) and acylase (trademark: Acylase Amano 15000) (900 mg) were added to the solution. The reaction mixture was stirred at 37° C. overnight, during which period the pH was maintained at 7.5 by an addition of 1N aqueous sodium hydroxide solution. The precipitates were collected by filtration, washed with water, and dried to give Object Compound (4.75 g).

mp: >192° C.

IR (Nujol): 3400, 1605, 1584, 1512, 888, 840 cm$^{-1}$

NMR (D$_2$O+NaOD, δ): 2.65–3.15 (2H, m), 3.49 (1H, dd, J=7.38 Hz, 5.72 Hz), 7.12 (1H, dd, J=8.24 Hz, 1.70 Hz), 7.36 (1H, d, J=1.6 Hz), 7.42 (1H, d, J=8.22 Hz)

Preparation 7

To an ice-cooled solution of Starting Compound (4.58 g) and methyl iodide (7.8 ml) in THF (40 ml) was added 60% sodium hydride (1.87 g) under nitrogen atmosphere. The mixture was stirred at room temperature overnight. Water was added to the mixture and THF was evaporated. Ether and water were added and the aqueous layer was separated. The organic layer was washed with water again. These aqueous layers were combined and acidified with 6N hydrochloric acid to pH 2 and the separated oil was extracted with ethyl acetate. The extract was washed with an aqueous sodium chloride solution, dried over magnesium sulfate and evaporated to give Object Compound as an oil (4.20 g).

IR(CHCl$_3$): 2600, 1700 cm$^{-1}$
NMR(CDCl$_3$, δ): 1.34 and 1.41(9H, s); 2.22(6H, s), 2.69 and 2.76(3H, s); 2.9–3.3(2H, m);

4.64(dd, J=10.9Hz and 4.5Hz)  
4.84(dd, J=10.7Hz and 5.2Hz) } (1H);

6.9–7.1(3H, m), 8.83(1H, s)

Preparation 8

The object compound was obtained according to a similar manner to that of Preparation 1.

mp: 119.0°–121.5° C.

IR (Nujol): 3370, 1718, 1690, 1526, 818 cm$^{-1}$

NMR (DMSO-d$_6$, δ): 1.26, 1.31 (9H, s); 2.70–3.15 (2H, m); 4.00–4.10 (1H, m); 7.10–7.30, 7.45–7.60 (4H, m); 12.70 (1H, br s)

Preparation 9

To an ice-cooled solution of Starting Compound (5.00 g) in methylene chloride (50 ml) were added TEA (2.29 ml) and pivaloyl chloride (2.03 ml). The mixture was stirred for 35 minutes at the same temperature and N-methylbenzylamine (1.81 g) was added to the solution. The solution was stirred for 25 minutes under ice-cooling and for additional 1.5 hours. After concentration, water and ethyl acetate were added to the residue and the separated organic layer was washed successively with an aqueous sodium hydrogen carbonate solution, water, 0.5N hydrochloric acid, and an aqueous sodium chloride solution, and dried over magnesium sulfate. After concentration, the crystalline residue (7.10 g) was washed with diisopropyl ether, collected by filtration and dried to give Object Compound (5.29 g).

mp: 103.0°–106° C.

IR (Nujol): 3390, 1690, 1638, 814, 730, 710 cm$^{-1}$

NMR (DMSO-d$_6$, δ): 1.21, 1.32 (9H, s); 2.90, 2.94 (3H, s); 2.70–3.05 (2H, m); 4.40–4.75 (3H, m); 7.05–7.65 (9H, m)

Preparation 10

The object compound was obtained according to a similar manner to that of Preparation 2.

mp: 126°–127° C.

IR (Nujol): 1680, 1645 cm$^{-1}$

NMR (CDCl$_3$, δ): 1.05, 1.19, 1.22 and 1.37 (9H, s); 2.18, 2.20 and 2.22 (6H, s); 2.83, 2.85 and 2.89 (6H, s); 2.9–3.25 (2H, m); 4.36–4.75 (2H, m); 4.95–5.03 and 5.30–5.45 (1H, m); 6.85–7.3 (8H, m)

Preparation 11

To an ice-cooled solution of Starting Compound (2.00 g) in ethyl acetate (7.5 ml) was added a solution (15 ml) of 4N-hydrochloric acid in ethyl acetate. The solution was stirred at the same temperature for 35 minutes and concentrated. Methylene chloride and an aqueous sodium hydrogen carbonate were added to the residue, and the organic layer was separated, was dried over magnesium sulfate, and concentrated to 5 ml volume (Solution I).

To an ice-cooled solution of Boc-(2S,4R)-Pro(4OH)-OH (1.06 g) in methylene chloride (15 ml) in another reaction vessel were added TEA (0.70 ml) and pivaloyl chloride (0.62 ml), and the mixture was stirred for 15 minutes at the same temperature. To this solution was added the solution prepared above (Solution I), and the resulting solution was stirred for an hour under ice-cooling and was left standing overnight at room temperature.

N,N-Dimethyl-1,3-propanediamine (0.23 ml) was added to the solution, and the mixture was stirred for an hour at room temperature. After concentration, ethyl acetate and water were added to the residue and the organic layer was washed successively with an aqueous sodium hydrogencarbonate solution, water, 0.5N hydrochloric acid, water and an aqueous sodium chloride solution, and was dried over magnesium sulfate. Evaporation of the solvent gave Object Compound (2.43 g) as an amorphous solid.

IR (CHCl$_3$): 3400–3260, 2960, 2930, 1625 cm$^{-1}$

NMR (DMSO-d$_6$, δ): 1.19, 1.38 (9H, s); 1.50–2.10 (2H, m), 270–3.10 (5H, m); 3.15–3.50 (2H, m); 4.05–5.05 (6H, m); 7.00–7.65 (8H, m); 8.25–8.40 (1H, m)

MASS: M$^+$ 550

Preparation 12

The object compound was obtained according to a similar manner to that of the former half of Preparation 11.

--- mp: 219–221° C.
IR(Nujol): 2750, 1650, 1550 cm$^{-1}$
NMR(DMSO-d$_6$, δ): 2.15(3H, s), 2.19(3H, s), 2.5 (6H, m), 2.85–3.0(1H, m), 3.17–3.35(1H, m), $\left\{ \begin{array}{l} 3.97(J=16.2Hz) \text{ and } 4.33(J=16.2Hz) \\ 4.39(J=14.7Hz) \text{ and } 4.51(J=14.7Hz) \end{array} \right\}$ (1H), 4.65(1H, dd, J=4.5Hz), 6.9–7.1(5H, m), 7.3(3H, m), 9.5(2H, br)

---

Preparation 13

The object compound was obtained according to a similar manner to that of the latter half of Preparation 11.

IR (CHCl$_3$): 3450, 1690, 1660 (sh), 1640 cm$^{-1}$

NFER (DMSO-d$_6$, δ): 1.09, 1.21, 1.27, 1.28, 1.37 and 1.38 (9H, s); 1.2–1.4, 1.4–1.6, 2.0–2.2 (2H, m); 1.99 and 2.13 (6H, s); 2.6–2.8 (4H, m); 3.0 (3H, m); 3.2–3.45 (3H, m); 4.1–4.7 (4H, m); 5.0 (1H, m); 5.4–5.6 (1H, m); 6.8–7.3 (8H, m)

Preparation 14

To an ice-cooled solution of Starting Compound (2.20 g) in ethyl acetate (7.5 ml) was added a solution (15 ml) of 4N-hydrogen chloride in ethyl acetate. The solution was stirred at the same temperature for two hours. After concentration, the residue was crystallized from ether to give Object Compound (1.59 g).

mp: 168.0°–175.0° C.

IR (Nujol): 3270, 1640 cm$^{-1}$

NMR (DMSO-d$_6$, δ): 1.60–1.90, 2.10–2.40 (2H, m); 2.80, 2.93 (3H, s); 2.70–3.40 (4H, m); 4.05–4.75 (4H, m); 4.85–5.10 (1H, m); 5.50–5.60 (1H, m); 7.00–7.65 (8H, m); 8.30–8.80, 9.60–10.15 (2H, br s); 9.17 (1H, d, J=8.08HZ)

Preparation 15

The object compounds were obtained according to a similar manner to that of Preparation 1.

(1) IR (Nujol): 3350, 1720, 1690, 1530, 1415, 1240 cm$^{-1}$

NMR (DMSO-d$_6$, δ): 1.32 (9H, s), 2.25 (3H, s), 2.7–3.0 (2H, m), 3.95–4.1 (1H, m), 6.85–7.15 (4H, m), 12.57 (1H, br s)

MASS: M+1 280, M$^+$ 279

(2) IR (CHCl$_3$): 2960, 1720, 1510 cm$^{-1}$

NMR (DMSO-d6, δ): 1.25, 1.31 (18H, s); 2.65–3.05 (2H, m); 3.95–4.15 (1H, m); 7.00–7.35 (5H, m); 12.58 (1H, br s)

MASS: M$^+$ 321

Preparation 16

The object compounds were obtained according to a similar manner to that of Preparation 2.

(1) mp: 74°–77° C.

IR (Nujol): 3390, 1691, 1642 cm$^{-1}$

NMR (DMSO-d$_6$, δ): 1.23, 1.28, 1.35 (9H, s); 2.24, 2.26 (3H, s); 2.65–2.95 (5H, m); 4.30–4.70 (3H, m); 6.90–7.40 (10H, m)

MASS: M$^+$ 382

(2) IR (CHCl$_3$): 3310, 2960, 1708, 1640 cm$^{-1}$

NMR (DMSO-d$_6$, δ): 1.25, 1.33 (18H, s); 2.70–2.90 (5H, m); 4.35–4.65 (3H, m); 6.95–7.40 (10H, m)

MASS: M$^+$ 424

Preparation 17

The object compounds were obtained according to a similar manner to that of Preparation 3.

(1) mp: 135°–138° C.

IR (Nujol): 3450, 1651, 1610 cm$^{-1}$

NMR (DMSO-d$_6$, δ): 2.28, 2.31 (3H, s); 2.61, 2.68 (3H, s); 2.85–3.20 (2H, m); 3.90–4.05, 4.35–4.70 (3H, m); 7.05–7.40 (9H, m); 8.48 (3H, s)

(2) IR (Nujol): 1645, 1580 cm$^{-1}$

NMR (DMSO-d$_6$, δ): 1.23, 1.29 (9H, s); 2.54 (3H, s); 2.85–3.20 (2H, m); 4.25–4.65 (3H, m); 7.05–7.40 (9H, m); 8.47 (3H, br s)

Preparation 18

The object compounds were obtained according to a similar manner to that of Preparation 4.

(1) IR (CHCl$_3$): 3320, 2900, 1680, 1640 cm$^{-1}$

NMR (DMSO-d$_6$, δ): 1.25, 1.39 (9H, s); 1.55–2.10 (2H, m); 2.26 (3H, s); 2.77, 2.85 (3H, s); 2.65–3.10 (2H, m); 3.15–3.50 (2H, m); 4.05–5.05 (6H, m); 6.90–7.35 (9H, m); 8.25–8.40 (1H, m)

MASS: M$^+$ 495

(2) IR (CHCl$_3$): 3420, 3320, 2970, 1690–1630 cm$^{-1}$

NMR (DMSO-d$_6$, δ): 1.24, 1.39 (18H, s); 1.55–2.05 (2H, m); 2.65–3.05 (5H, m); 3.15–3.45 (2H, m); 4.05–5.00 (6H, m); 6.95–7.35 (9H, m); 8.25–8.35 (1H, m)

MASS: M$^+$ 537

Preparation 19

To an ice-cooled solution of Starting Compound (3.00 g) in methylene chloride (12 ml) was added 12 ml of 4N hydrochloric acid solution in ethyl acetate. The resulting mixture was stirred at this temperature for one and half an hour. The solvent was evaporated and the residue was triturated with ether. The precipitates were filtered, washed with ether, and dried under vacuum to give Object Compound (2.81 g).

IR (Nujol): 3350–3200, 1641, 1566, 1548 cm$^{-1}$

NMR (DMSO-d$_6$, δ): 1.65–1.90, 2.20–2.40 (2H, m); 2.27 (3H, s); 2.76, 2.84 (3H, s); 2.70–3.45 (4H, m); 4.20–4.60 (4H, m); 4.80–5.05 (1H, m); 5.55 (1H, br s); 6.95–7.40 (9H, m); 8.59 (1H, br s); 9.15 (1H, d, J=7.6 Hz); 10.04 (1H, br s)

Preparation 20

The object compound was obtained according to a similar manner to that of Preparation 19.

IR (Nujol): 3350–3200, 1675, 1640, 1561, 1541 cm$^{-1}$

NMR (DMSO-d$_6$, δ): 1.25, 1.26 (9H, s); 1.70–1.95, 2.20–2.40 (2H, m); 2.75–2.80 (3H, s); 2.80–3.40 (4H, m); 4.20–4.65 (4H, m); 4.80–5.00 (1H, m); 5.57 (1H, br s); 7.00–7.40 (9H, m); 8.61 (1H, br s); 9.16 (1H, d, J=7.6 Hz); 10.01 (1H, br s)

EXAMPLE 1

Starting Compound (2.42 g) was dissolved in ethyl acetate (15 ml) and ice-cooled. To the solution was added 4N hydrochloric acid solution in ethyl acetate (30 ml) and the mixture was stirred for forty minutes at the temperature. After evaporation, the residue was dissolved in methylene chloride (50 ml). This solution was washed with saturated sodium hydrogencarbonate solution and separated. The aqueous layer was extracted with methylene chloride again and the extracts were combined, washed with brine, and dried over magnesium sulfate. Filtration gave a solution of the deprotected amine derived from Starting Compound (0.0826 m mol/g). A 24 ml portion of this solution was added to a solution of 1-(N,N-dimethylaminoethyl)indole-3-carboxylic acid (537 mg) and HOBT (270 mg) in dimethylformamide (15 ml). The mixture was ice-cooled and WSC.HCl (420 mg) was added. The mixture was stirred for one and half an hour at the temperature and for six hours at room temperature. TEA (0.14 ml) was added thereto and the mixture was stirred overnight at room temperature. The mixture was concentrated and the residue was diluted with water and sodium hydrogen carbonate solution. The mixture was extracted with methylene chloride twice and the combined extracts were washed with brine and dried over magnesium sulfate. After evaporation, the residue was subjected to a silica gel (25 g) column chromatography eluting with a mixed solvent of chloroform and methanol (from 2% to 5%, gradient). The main fraction were concentrated and the residue (0.25 g) was dissolved in THF (9 ml). The solution was ice-cooled and 4N hydrochloric acid in ethyl acetate (0.20 ml) was added and the mixture was concentrated. The residue was triturated with ether, filtered, and dried to give Object Compound (0.23 g).

NMR (DMSO-$d_6$, δ): 1.5–2.0 (2H, m), 2.14 (6H, s), 2.7–2.9 (9H m), 3.12 and 3.16 (3H, s), 3.6–4.0 (4H, m), 4.3–4.6 (3H, m), 4.73 (2H, br s), 5.1 (1H, m), 5.5 (1H, m), 6.87–7.3 (10H, m), 7.7 (1H, m), 8.05 (2H, m), 10.91 (1H, br s)

MASS: $M^+$ 517

EXAMPLE 2

To an ice-cooled mixture of benzofuran-2-carboxylic acid (0.15 g), Starting Compound (0.45 g), and HOBT (0.12 g) in 9 ml of methylene chloride was added WSC (0.17 ml). The resulting solution was stirred at the same temperature for half an hour and overnight at room temperature. N,N-dimethyl-1,3-propanediamine (0.05 ml) was added thereto and the mixture was stirred for additional two hours. The mixture was evaporated and the residue was diluted with water and extracted with ethyl acetate. The organic layer was washed successively with saturated sodium hydrogencarbonate solution, water, 0.5N hydrochloric acid and brine, and dried over magnesium sulfate. After evaporation, the crude material was subjected to a silica gel (20 g) chromatography eluting with a mixed solvent of chloroform and methanol (from 1% to 2.5%, gradient). Concentration of the fractions and pulverization with diisopropyl ether gave Object Compound (0.40 g).

IR (Nujol): 3300, 1630, 1565 $cm^{-1}$

NMR (DMSO-$d_6$, δ): 1.85–2.15 (2H, m), 2.15–3.10 (2H, m), 2.76, 2.77 and 2.89 (3H, s), 3.60–5.20 (8H, m), 6.85–7.80 (13H, m), 8.50–8.80 (1H, m)

MASS: $M^+$ 594

EXAMPLE 3

To a suspended mixture of benzofuran-2-carboxylic acid (0.31 g) and HOBT (0.26 g) in methylene chloride (10 ml) was added WSC.HCl (0.37 g) at room temperature. The resulting solution was stirred for thirty minutes. During this period, a solution of Starting Compound (1.0 g) and TEA (0.29 ml) in methylene chloride (10 ml) in an another reaction vessel under ice-cooling. The two reaction mixture were mixed at room temperature and the resulting mixture was stirred at room temperature overnight. After evaporation, the residue was diluted in water and extracted with ethyl acetate. The organic layer was washed successively with sodium hydrogen carbonate solution, water, 1N hydrochloric acid and brine, and dried over magnesium sulfate. After evaporation, the crude product was purified on a silica gel (54 g) column eluting with a mixed solvent of methylene chloride and methanol (50:1 to 20:1, gradient elution). The purified material was crystallized with a mixed solvent of ethyl acetate and diisopropyl ether to give Object Compound (0.77 g).

mp: 137°–139° C.

IR (Nujol): 3400, 3250, 3100, 1630, 1570, 1420 $cm^{-1}$

NMR (DMSO-$d_6$, δ): 1.7–1.9 (1H, m); four singlet at 2.05, 2.10, 2.11 and 2.17 (6H); 2.2–2.4 (1H, m); four singlets at 2.60, 2.64, 2.73 and 2.79 (3H); 2.8–3.5 (2H, m); 3.6–4.1 (2H, m); 4.3–5.2 (6H, m), 6.6–7.8 (14H, m); 8.54 and 8.73 (1H, d, J=8 Hz)

MASS: $M^+$ 553

EXAMPLE 4

The object compounds were obtained according to a similar manner to that of Example 3.

(1) IR (Nujol): 3300, 1625, 1560 $cm^{-1}$

NMR (DMSO-$d_6$, δ): 1.70–2.20 (2H, m); 2.25 (3H, s); 2.20–3.10 (5H, m); 3 50–5.25 (8H m); 6 70–7.90 (14H, m); 8.45–8.80 (1H, m)

MASS: $M^+$ 539

(2) IR (Nujol): 3280, 1620, 1560, 1508 $cm^{-1}$

NMR (DMSO-$d_6$, δ): 1.21, 1.22, 1.24 (9H, s); 1.60–2.45 (2H, m); 2.58, 2.72, 2.77 (3H, s); 2.75–3.10 (2H, m); 3.60–3.70, 3.75–4.10, 4.20–5.25 (8H, m); 6.75–7.85 (14H, m); 8.45–8.80 (1H, m)

MASS: $M^+$ 581

(3) mp: 171°–173° C.

IR (Nujol): 3400, 3250, 1667, 1630, 1561 $cm^{-1}$

NMR (DMSO-$d_6$, δ): 1.70–2.35 (2H, m); 2.12, 2.17 (6H, s); 2.60, 2.73, 2.79 (3H, s); 2.65–3.10 (2H, m); 3.60–5.20 (8H, m); 6.50–8.10 (13H, m); 8.50–8.85 (1H, m)

MASS: $M^+$ 569

EXAMPLE 5

To a solution of Starting Compound (3.20 g) in methylene chloride (32 ml) was added TEA (1.61 ml) under ice-cooling. To this solution was added a solution of MsCl (0.45 ml) in methylene chloride (5 ml) maintaining the temperature below 6° C. After stirring for three hours. TEA (1.61 ml) was added and a solution of MsCl (0.45 ml) in methylene chloride (5 ml) was added dropwise. The mixture was stirred for additional half an hour and washed with water. The organic layer was dried over magnesium sulfate, and evaporated to give Object Compound (3.61 g) as an amorphous solid.

IR ($CHCl_3$): 3300, 1680, 1630, 1175 $cm^{-1}$

NMR (DMSO-$d_6$, δ): 1.9–2.3 (2H, m), 2.10, 2.12 and 2.17 (6H, s), 2.64, 2.74, 2.78 (3H, 3s); 2.6–2.3 (2H, m), 3.26 and 3.30 (3H, 2s); 3.8–5.0 (5H, m); 5.1–5.4 (2H, m); 6.5–7.8 (13H, m); 8.67 and 8.81 (1H, 2d, J=8 Hz)

EXAMPLE 6

To a solution of Starting Compound (3.60 g) in DMSO (18 ml), sodium azide (0.74 g) was added. The solution was heated at 70° C. for 16.5 hours. After cooling, ethyl acetate (100 ml) was added and the solution was washed with water (three times) and brine. The organic layer was dried over magnesium sulfate and concentrated to give the concentrate of Intermediate Compound (ca. 50 ml). To the solution was added triphenylphosphine (1.49 g), then heated at 50° C. for 2 hours. After adding water (0.31 ml), the mixture was heated at 65° C. for 4.5 hours. The precipitates were filtered, subjected to a silica gel columnchromatography (150 g) and eluted with chloroform-methanol (from 20:1 to 5:1, gradient). The main fractions were evaporated to give Object Compound (1.97 g). In ethanol, Starting Compound (0.43 g) was dissolved under heating. After ice-cooling, 4N-HCl/ DOX (0.21 ml) was added and the solution was evaporated. The residue was pulverized with diisopropyl ether, filtered and dried to give Object Compound (0.40 g).

mp: 130° C. (dec.)

IR (Nujol): 3450, 3250, 1625, 1565 cm$^{-1}$

NMR (DMSO-d6, δ): 1.6–2.2 (2H, m), 2.10, 2.13 and 2.18 (6H, 3s), 2.66 and 2.76 (3H, 2s), 2.6–3.0 (2H, m), 3.7–5.3 (7H, m), 6.6–7.9 (13H, m), 8.39 (3H, s), 9.04 (1H, m)

We claim:

1. A process for preparing a compound of the formula:

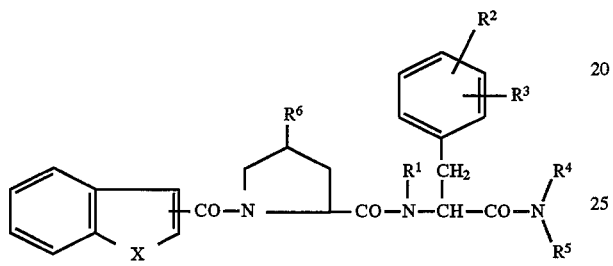

wherein
$R^1$ is hydrogen or lower alkyl,
$R^2$ is lower alkyl or halogen,
$R^3$ is hydrogen, lower alkyl or halogen,
$R^4$ is lower atkyl,
$R^5$ is ar(lower)alkyl,
$R^6$ is amino or optionally protected hydroxy, and
X is O, S or N—$R^7$ in which $R^7$ is N,N-di(lower) alkylamino(lower)alkyl, or a pharmaceutically acceptable salt thereof, which comprises reacting a compound of the formula:

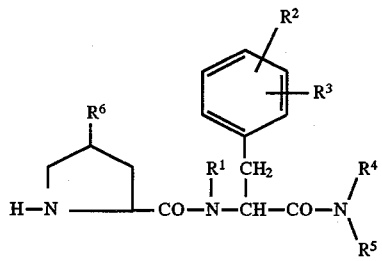

wherein $R^1$, $R^2$, $R^3$, $R^4$, $R^5$ and $R^6$ are each as defined above, or its reactive derivative at the amino group or a salt thereof, with a compound of the formula:

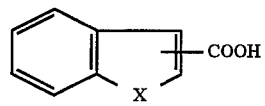

wherein X is as defined above, or its reactive derivative at the carboxy group or a salt thereof.

* * * * *